United States Patent [19]

Nagy et al.

[11] Patent Number: 5,252,604
[45] Date of Patent: Oct. 12, 1993

[54] COMPOSITIONS OF RETINOIC ACIDS AND TOCOPHEROL FOR PREVENTION OF DERMATITIS

[75] Inventors: Christa F. Nagy, Wyckoff; Timothy W. Quick, Clifton; Stanley S. Shapiro, Livingston, all of N.J.

[73] Assignee: Hoffmann-La Roche Inc., Nutley, N.J.

[21] Appl. No.: 911,606

[22] Filed: Jul. 10, 1992

[51] Int. Cl.$^5$ ............................................. A61K 31/20
[52] U.S. Cl. ..................................... 514/559; 514/859
[58] Field of Search ................................. 514/458, 559

[56] References Cited

U.S. PATENT DOCUMENTS 4,843,096  6/1989  Stiefel ................................... 514/559
4,900,550  2/1990  Lowry ................................. 424/195.1

OTHER PUBLICATIONS

Chemical Abstracts 114:88699r (1991).

Primary Examiner—Leonard Schenkman
Attorney, Agent, or Firm—George M. Gould; William H. Epstein; Catherine R. Roseman

[57] ABSTRACT

Compositions of retinoic acids and tocopherols which may be applied topically without producing retinoic acid-induced skin irritation.

8 Claims, 2 Drawing Sheets

COMPOSITIONS OF RETINOIC ACIDS AND TOCOPHEROL FOR PREVENTION OF DERMATITIS

BACKGROUND OF THE INVENTION

Retinoic acids such as 13-cis-retinoic acid and all-trans-retinoic acid are known to have beneficial dermatological effects, i.e. on human skin, and may be applied to retard the effects of photoaging on skin, or to combat acne, or in general to improve skin quality. However, repeated topical application of retinoic acids to human skin for these dermatological purposes may initially cause transient skin irritation (dermatitis) which may be characterized by erythema, scaling, pruritus, and sensations similar to sunburn (1,2). This problem is described in U.S. Pat. No. 4,888,342. Such results are also observed in animals after repeated topical dosing with retinoic acids.

The inflammatory component of retinoic acid induced skin irritation in animals can be demonstrated histologically by an influx of inflammatory cells into the skin. The effect can be quantified biochemically from measurement of increased myeloperoxidase (MPO) activity in skin biopsy punches (3) (MPO is a marker enzyme for neutrophils). In mice, for example, topical retinoic acid induced skin irritation is characterized by an inflammatory response and, after repeated topical applications, epidermal hyperproliferation.

Tocopherols, for example alpha tocopherol (Vitamin E), have long been recognized for their properties as free radical scavenging antioxidants (4). Also, it has been demonstrated that Vitamin E taken orally at a dose of 800 mg can reduce the toxic side effects of 13-cis-retinoic acid (100 mg/m$^2$) in patients who were treated with this retinoic acid for myelodysplastic syndrome (5).

SUMMARY OF THE INVENTION

The problem of retinoic acid induced dermatitis resulting from topical retinoic acid application for dermatological effects can be overcome by adding a tocopherol such as alpha tocopherol to the topical composition.

The subject invention therefore is directed to a composition of a retinoic acid and a tocopherol which is applied topically and has the desired dermatological effects of retinoic acid application with reduction in the undesired side effects of retinoic acid induced dermatitis or inflammation.

DETAILED DESCRIPTION OF THE INVENTION

Figure 1:
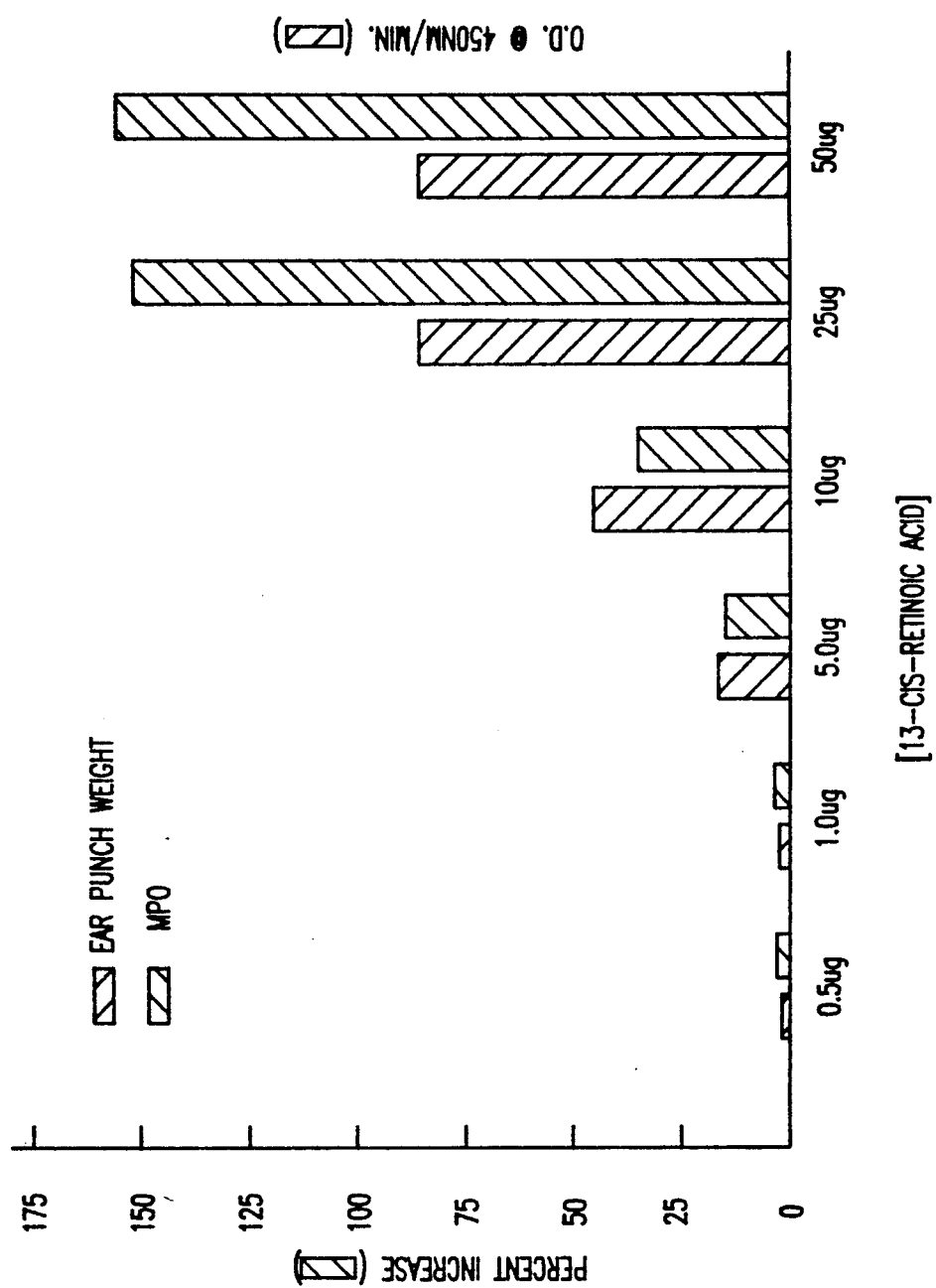
FIG. 1: Topical irritation by 13-cis-retinoic acid in the mouse after eight (8) days. Skin irritation is measured by MPO activity (hatched upwards bar), and ear punch biopsy weight (hatched downwards bar). This graph demonstrates increasing irritant reactions to 13-cis-retinoic acid applied alone.

This invention is drawn to compositions of a tocopherol and a retinoic acid, which compositions have the therapeutic dermatological effects of a retinoic acid, and avoid much of the skin irritation induced by retinoic acid. The retinoic acid is present in an amount effective for treating dermatological disorders. The tocopherol is present in an amount sufficient to reduce retinoic acid-induced skin irritation. Retinoic acid includes the retinoid all-trans retinoic acid, geometric isomers such as 13-cis-retinoic acid, and pharmaceutically acceptable esters. Also contemplated are those natural or synthetic retinoic acid analogues which have beneficial therapeutic effects on skin as described.

The liquid compositions can be applied in accordance with this invention to human skin in conventional topical compositions. The dermatological effects of retinoic acids are well known. These effects make retinoic acids useful in a range of applications. For example, retinoic acids may be used to treat dermatological disorders such as acne, photodamage (i.e., wrinkling) and epithelial carcinomas which can be reduced in size by treatment.

These topical compositions are in the form of liquid compositions suitable for topical administration (including for example creams, gels, ointments, microemulsions, shampoos, and solutions).

Any amount of retinoic acid effective to treat dermatological disorders, for example, acne and photodamage, is contemplated. Specifically, the concentration of retinoic acid, in particular 13-cis-retinoic acid, may be in a range of about 0.05% to about 0.2% by weight per volume of liquid composition, and the concentration of tocopherol, in particular alpha-tocopherol, may be in a range from about 0.005% to 5.0% by weight per volume of the liquid composition. In particular, the alpha tocopherol may be present in a range of about 0.01% to about 5.0% by weight per volume.

This invention provides a method for topically applying retinoic acid to skin to treat dermatological disorders without inducing skin irritation caused by said retinoic acid by applying topically a liquid composition containing retinoic acid and alpha tocopherol, said composition being applied in an amount sufficient to produce the dermatological effects of said retinoic acid, and said alpha tocopherol being present in an amount sufficient to reduce the skin irritation caused by the retinoic acid. Also included is a method for providing a composition for topical application to treat dermatological disorders by mixing retinoic acid with an amount of alpha tocopherol sufficient to reduce the skin irritation induced by the retinoic acid, which itself is present in a dermatologically effective amount. Alpha-tocopherol and 13-cis-retinoic acid are preferred in these methods. Effective amounts of retinoic acid for a particular application are well-known in the art (U.S. Pat. Nos. 5,075,333; 4,888,342; 4,487,782; 4,603,146; and 4,877,805), or can be determined empirically by assays or tests such as those described in Examples 1 and 2. The amount of alpha tocopherol sufficient to reduce skin irritation can be similarly determined. The amounts used may be those above for the liquid compositions described above, specifically about 0.01% to about 5.0% by weight tocopherol and about 0.05% to about 0.2% by weight retinoic acid.

These liquid compositions may be applied to the skin of the body, in particular face, legs, arms and hands. They may be administered in any conventional topical preparations, i.e., in combination with any suitable conventional carrier useful for topical administration. Such topical compositions include cream, ointment, soap, solutions, lotions, emulsions, shampoo and any other conventional topical preparations. In formulating the preparations, any conventional non-toxic dermatologically acceptable base or carrier in which these compositions are stable is acceptable.

Preferred compositions may contain conventional cosmetically active ingredients. Examples of conventional cosmetically active materials are sunscreens, penetration enhancers, moisturizers, surfactants, emollients, colorants, conditioners, bacteriocides, astringents, detergents and other such materials. Any conventional sunscreen may be included in the claimed composition.

These topical composition can contain any conventional excipients and additives commonly used in preparing skin compositions. Among the conventional additives or excipients are preservatives, thickeners, perfumes and the like. In addition, conventional antioxidants such as butylated hydroxy anisoles (BHA), ascorbyl palmitate, propyl gallate, citric acid, butylated hydroxytoluene (BHT), ethoxyquin, and the like can be incorporated into these compositions. These compositions may contain thickening agents, solubilizers, humectants, emulsifiers and viscosity stabilizers, any of which are well known in the art. In addition, these compositions can contain flavoring, perfuming, or coloring agents conventionally used.

The topical compositions should be applied to the skin with a frequency to be determined for an individual patient. In general, the particular regimen for application will depend on the age, weight, and skin condition of the individual. However, an exemplary regimen for retinoic acid application to reverse sun damage and reduce wrinkling is at least one application to the skin at least 2 to 3 times weekly for at least 5 months, and thereafter as needed to maintain skin elasticity. For acne treatment, an exemplary regimen is one or more applications daily for about four to six weeks.

This invention is further illustrated in the following examples. These examples are for illustration only and are intended not to limit the claimed invention.

EXAMPLE 1

Example 1 demonstrates that skin irritation caused by topical application of retinoic acid can be reduced if the retinoic acid is applied with alpha-tocopherol. Skin irritation is determined from the amount of inflammation developed in the area of application, specifically the ear. The amount of inflammation is related to the increase in the number of inflammatory cells (neutrophils) in ear tissues caused by retinoic acid application. Increase in neutrophils is directly proportional to MPO activity (MPO is a neutrophil marker enzyme), which activity is quantified colorimetrically by adding substrate and measuring optical density resulting from the MPO reacting on the substrate. Increased ear weight due to inflammation is another measure of the amount of inflammation caused by retinoic acid application.

Male CD-1 mice (5 weeks old) were dosed topically on the dorsal side of the right ear daily for eight (8) days with 25 $\mu$l of an acetone solution containing both 0.08% (20 $\mu$g/25 $\mu$l) 13-cis-retinoic acid and various doses of alpha tocopherol (Vitamin E), ranging from 0.01% to 5.0% (2.5 $\mu$g to 1.2 mg). Eight animals per group were used. Control groups were treated either with a solution of 0.08% 13-cis-retinoic acid alone or with the solvent (acetone). On day nine (9) the animals were sacrificed by $CO_2$ inhalation and biopsy punches (6 mm diameter) were removed from the treated ears. The biopsy punches were weighed, homogenized, and the homogenate was assayed for MPO activity, according to the method of Bradley, et al. (3) which was adapted to 96 well microtiter plates. MPO activity was determined by measuring the change in optical density of the reaction mixture at 450 nm in a 96 well plate reader (SLT Lab instruments) over a period of two minutes. The data are expressed as percent inhibition of alpha tocopherol (Vitamin E) treated groups relative to the control groups according to the formula[1]:

$$\% \text{ inhibition} = \frac{\Delta O.D. \ RA - \Delta O.D. \ (RA + E)}{\Delta O.D. \ RA - \Delta O.D. \ \text{control}} \times 100$$

[1]$\Delta$O.D. RA is the change in O.D. per minute at 450 nm for the group treated with retinoic acid. $\Delta$O.D. (RA+E) is the change in O.D. per minute at 450 nm for the group treated with retinoic acid and alpha tocopherol. $\Delta$O.D. control is the change in O.D. per minute at 450 nm for the vehicle control group.

Figure 2:
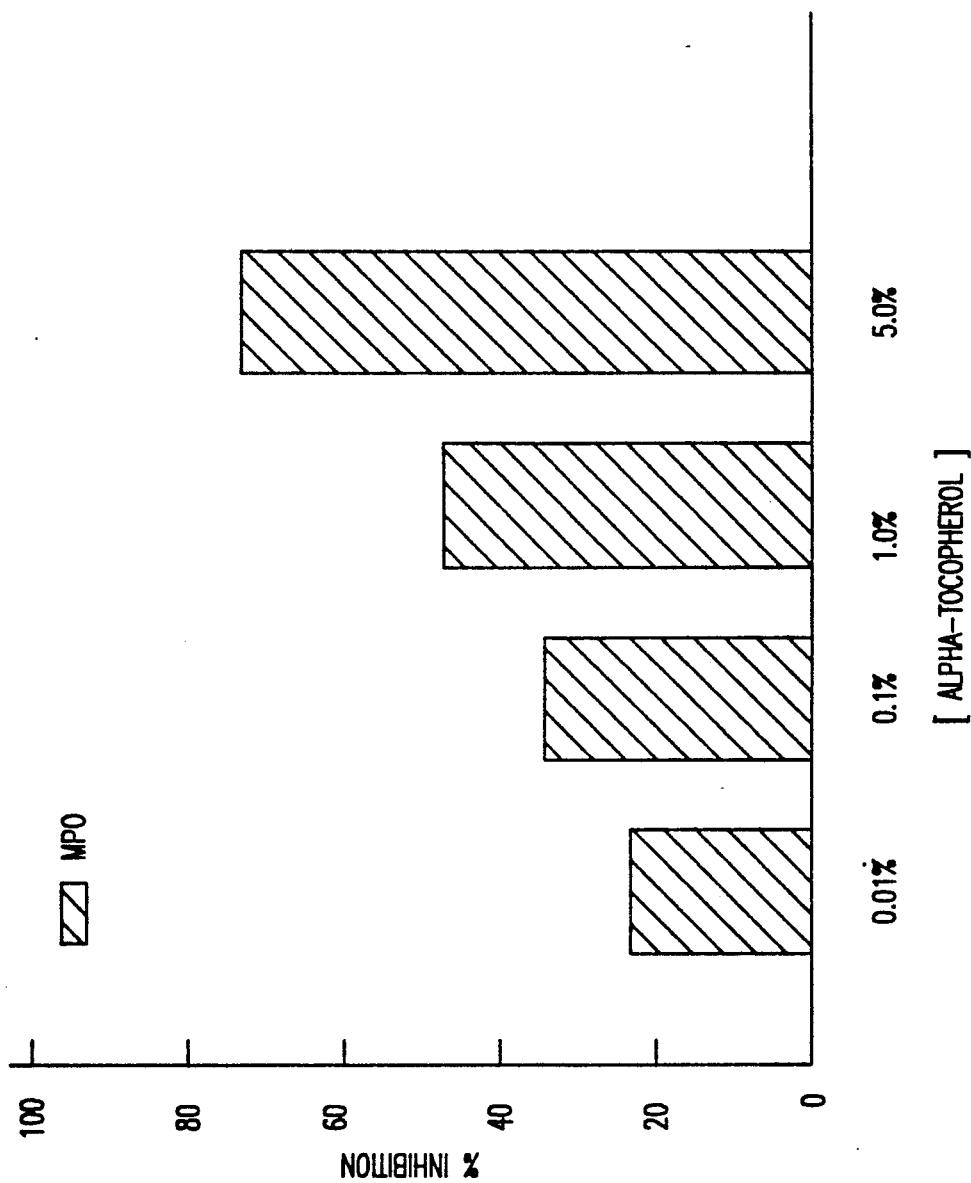
FIG. 2: Inhibition of 13-cis-retinoic acid induced mouse skin irritation by topical alpha tocopherol. Percent inhibition of MPO (hatched upwards bars) with increasing concentrations of alpha tocopherol 13-cis-RA, 20.0 µg.

Topical application of 13-cis-retinoic acid for eight (8) days to mouse ears resulted in a dose related increase in infiltration of polymorphonuclear neutrophils, as indicated by the increase in MPO activity. Ear wet weight was also increased in a dosed-related manner and this increase was partially due to ear inflammation and epidermal hyperproliferation in response to the retinoic acid. FIG. 1 shows MPO activity and wet weight in mouse ear punches increasing with increasing doses of 13-cis-retinoic acid. MPO activity is a measure of the inflammatory response, as discussed above. Alpha-tocopherol, at concentrations from 0.01% to 5.0%, inhibited the retinoic acid-induced increase in MPO activity (neutrophil infiltration) in a dose related manner. FIG. 2 shows retinoic acid-induced MPO activity in mouse ears decreasing with increasing doses of alpha-tocopherol. Maximum inhibition (70%) of 13-cis-retinoic acid-induced neutrophil infiltration was obtained at an alpha-tocopherol concentration of 5.0%. These data clearly demonstrate that topical alpha tocopherol (optimum doses) can ameliorate the inflammatory component induced by repeated topical application of 13-cis-retinoic acid.

EXAMPLE 2

The liquid compositions described herein can be provided for topical application in creams, lotions, shampoos, and any other topical formulation. The percentages given in these examples are percent by weight based on the total volume of the liquid composition. Specific formulations are described below. However, any conventional formulation can be used for the claimed composition.

a. Liposomal Formulations

| Ingredient | % by Weight |
|---|---|
| Isotretinoin | 0.050–1.000 |
| Vitamin E | 0.005–5.000 |
| L-α-Dimyristyl Phosphatidyl Choline | 0.062 |
| Cholesterol | 0.062 |
| T-Butyl Alcohol | 31.089 |
| Lactose | 6.000 |
| Purified Water q.s. to | 100.000 | b. Water in Oil Cream

| Ingredient | % by Weight |
|---|---|
| Isotretinoin | 0.050–1.000 |

-continued

| Ingredient | % by Weight |
| --- | --- |
| Vitamin E | 0.005-5.000 |
| Propylene Glycol Dicaprylate/Dicaprate and Stearalkonium Bentonite (and) Propylene Carbonate | 20.000 |
| Caprylic/Capric Triglyceride | 20.000 |
| Isostearyl Diglyceryl Succinate | 5.000 |
| Purified Water q.s. to | 100.000 | c. Hair Conditioning Gel

| Ingredient | % by Weight |
| --- | --- |
| Isotretinoin | 0.050-1.000 |
| Vitamin E | 0.005-5.000 |
| PEG-7-Glyceryl Cocoate | 10.000 |
| Ethanol, Anhydrous | 24.000 |
| Methyl pyrol | 5.000 |
| Dimyristyl Phosphatidyl Choline | 0.030 |
| Sodium Ascorbate | 0.030 |
| Citric Acid | 0.100 |
| Carbomer 940 | 0.500 |
| B-Alanine | 0.500 |
| Purified Water q.s. to | 100.000 | d. Oil in Water Cream

| Ingredient | % by Weight |
| --- | --- |
| Isotretinoin | 0.05-1.00 |
| Vitamin E | 0.005-5.00 |
| Propylene Glycol Dicaprylate/Dicaprate | 8.95 |
| Stearyl Alcohol | 0.75 |
| Glyceryl Stearate | 4.00 |
| Ceteareth-12 | 0.50 |
| Ceteareth-20 | 0.50 |
| Propylparaben | 0.10 |
| Methylparaben | 0.15 |
| Disodium Edetate | 0.03 |
| Glycerin | 5.00 |
| Purified Water q.s. to | 100.000 | e. Cream (Anhydrous)

| Ingredient | % by Weight |
| --- | --- |
| Isotretinoin | 0.05-1.00 |
| Vitamin E | 0.005-5.00 |
| Caprylic/Capric/Stearic Triglyceride | 29.00 |
| Glyceryl Cocoate (and) Ceteareth-25 | 43.00 |
| Propylene Glycol Dicaprylate/Dicaprate | 8.95 |
| Mineral Oil q.s. to | 100.000 | f. Oil in Water Microemulsion

| Ingredient | % by Weight |
| --- | --- |
| Isotretinoin | 0.05-1.00 |
| Vitamin E | 0.005-5.00 |
| DEA-Oleth-3 Phosphate | 8.95 |
| Oleth-20 | 1.00 |
| Oleth-10 | 15.00 |
| Mineral Oil | 4.00 |
| Propylene Glycol Dicaprylate/Dicaprate | 8.00 |
| BHT | 0.03 |
| Hexetidine | 0.10 |
| Citric Acid | 0.05 |
| Sodium Ascorbate | 0.10 |
| Sorbic Acid | 0.10 |
| Glycerin | 5.00 |

-continued

| Ingredient | % by Weight |
| --- | --- |
| Purified Water q.s. to | 100.000 | g. Topical Solution

| Ingredient | % by Weight |
| --- | --- |
| Isotretinoin | 0.050-1.000 |
| Vitamin E | 0.005-5.000 |
| PEG-7-Glyceryl Cocoate | 10.000 |
| Ethanol, Anhydrous | 25.000 |
| Purified Water q.s. to | 100.000 |

REFERENCES

1. Weiss, J. S., Ellis, C. N., Headington, J. T., Tincoff, T., Hamilton, T. A., and Voorhees, J. J., Topical tretinoin improves photoaged skin: A double-blind vehicle controlled study. JAMA 1988; 259:527-32.
2. Weiss, J. S., Ellis, C. N., Headington, J. T., and Voorhees, J. J., Topical tretinoin in the treatment of aging skin. J. Am. Acad. Dermatol. 1988; 19:169-75.
3. Bradley, P. P., Priebat, D. A., Christensen, R. D. and Rothstein G. Measurement of cutaneous inflammation: Estimation of neutrophil content with an enzyme marker. J. Invest. Dermatol. 1982; 78:206-209.
4. Witting, L. A. Vitamin E and Lipid Anti-Oxidants in Free Radical Initiated Reactions, in: Free Radicals in Biology, Vol. IV (W. A. Pryor ed.) Academic Press, 1980.
5. Besa, E. C., Abrahm, J. L., Bartholomew, M. J., Hyzinski, M. and Nowell, P. C. Treatment with 13-cis-retinoic acid in transfusion-dependent patients with myelodysplastic syndrome and decreased toxicity with addition of alpha tocopherol. Amer. J. Med. 1990; 89:739-746.

We claim:

1. A liquid composition suitable for topical administration which comprises an amount of retinoic acid effective for treating dermatological disorders and an amount of alpha tocopherol sufficient to reduce the skin irritation caused by said retinoic acid.

2. A liquid composition suitable for topical administration which comprises about 0.05% to about 0.2% by weight retinoic acid and about 0.005% to about 5.0% by weight alpha tocopherol per volume of said liquid composition.

3. The composition of claim 1 wherein the retinoic acid is 13-cis-retinoic acid.

4. A liquid composition of claim 1 which comprises about 0.01% to about 5.0% alpha tocopherol by weight per volume of said liquid composition.

5. A method for topically applying retinoic acid to skin for dermatological purposes without inducing skin irritation caused by said retinoic acid which comprises applying a liquid composition containing retinoic acid and alpha tocopherol, said composition being applied in an amount sufficient to produce the dermatological effects of said retinoic acid, said alpha tocopherol being present in an amount sufficient to reduce the skin irritation caused by the retinoic acid.

6. The method of claim 5 wherein the amount of alpha tocopherol is about 0.01% to about 5.0% by weight per volume of said liquid composition.

7. The method of claim 5 wherein the retinoic acid is present in an amount from about 0.05% to about 0.2% by weight per volume of said liquid composition.

8. The method of claim 5 wherein the retinoic acid is 13-cis-retinoic acid.

* * * * *